United States Patent
Watts, Jr. et al.

[11] 3,996,261
[45] Dec. 7, 1976

[54] CYANOPOLYHALOANILINES

[75] Inventors: Lewis W. Watts, Jr.; Philip H. Moss, both of Austin, Tex.

[73] Assignee: Texaco Development Corporation, New York, N.Y.

[22] Filed: Nov. 6, 1975

[21] Appl. No.: 629,343

[52] U.S. Cl. .............................. 260/465 E; 71/103; 71/105; 71/121; 424/304; 424/330; 260/570.5 P; 260/573
[51] Int. Cl.² .............. C07C 121/78; C07C 121/80
[58] Field of Search ................ 260/465 E, 570.5 P, 260/573

[56] References Cited
UNITED STATES PATENTS

| | | | |
|---|---|---|---|
| 2,829,164 | 4/1958 | Hocklin | 260/570.5 |
| 3,714,046 | 1/1973 | Adams et al. | 260/570.5 X |

OTHER PUBLICATIONS
Beck et al., Chemical Abstracts, vol. 70, 11553d, (1968).

*Primary Examiner*—Lewis Gotts
*Assistant Examiner*—Dolph H. Torrence
*Attorney, Agent, or Firm*—Carl G. Ries; Thomas H. Whaley; James L. Bailey

[57] ABSTRACT

Novel polyhalo, N-substituted aniline compounds are prepared which have the following structural formula:

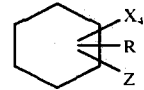

where R is selected from the group consisting of cyano, nitro, and alkyl sulfone. X is halo and Z represents a radical as follows:

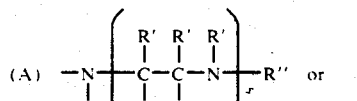

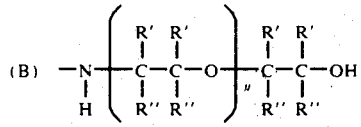

where R' and R" are hydrogen or lower alkyl, X is a number ranging from 1 to 5, and Y is 0–3. These compounds are prepared by reacting a polyhalo aromatic compound having the formula

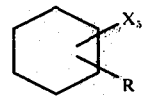

where X and R have a significance as just discussed with an appropriate polyamino reactant or aminohydroxy compound which additionally may contain either linkages. These new compounds have biological activity and are also useful as chemical intermediates.

5 Claims, No Drawings

CYANOPOLYHALOANILINES

BACKGROUND OF THE INVENTION

1. Field of the Invention

This invention pertains to new compositions of matter, their synthesis and their biological use.

2. Description of the Prior Art

Beck, G., Degenes, E., and Heitzer, H., Ann. Chem., 715, 47 (1968) discussed the chemistry of pentachlorobenzonitrile, and particularly reported the reaction of mono-functional amines such as ammonia, methylamine, dimethylamine, ethylamine, etc., with pentachlorobenzonitrile. However, this report deals with chemical transformations of pentachlorobenzonitrile with only mono-functional amino compounds. To date the reaction of pentachlorobenzonitrile or other pentahalo aromatics containing activating groups such as cyano, nitro, etc., with polyamines or amino compounds containing a further potentially reactive functional group such as hydroxy, are apparently not known in the art.

SUMMARY OF THE INVENTION

New compounds of the formula

where R is selected from the group consisting of cyano, nitro and lower alkyl sulfone, X is halo, and Z is a radical represented by (A)

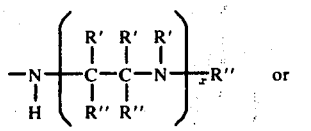   or (B)

where $R'$ and $R''$ are hydrogen or lower alkyl, $x$ is an integer ranging from 1 to 5, and $y$ is a number of 0–3.

These compounds are prepared by reacting an amino compound having a structural formula represented by

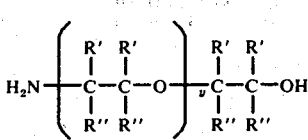

with a polyhalo aromatic compound having the formula

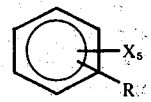

where X, R, $R'$, $R''$, and $x$ and $y$ have a significance as just set forth.

DESCRIPTION OF THE PREFERRED EMBODIMENT

The new anilines of my invention are prepared by the interaction of a pentahalo benzene compound also containing an additional activating group such as cyano, nitro, and lower alkyl sulfone with a polyamine or aminohydroxy reactant which optionally may also contain ether linkages. When the activating group is a lower alkyl sulfone, it is preferred that the alkyl group contain 1–4 carbon atoms. Preferred pentahalobenzene compounds are pentachlorobenzene reactants, and most preferably pentachlorobenzonitrile is a reactant.

The amine reactant may be chosen from ethylenediamine, diethylene-triamine, tetraethylene-pentamine, and like polyamines, aminoethanol, 2-(2-aminoethoxy)ethanol, and like aminoalkanols, and amino-alkoxy-alkanols. When the amine reactant also contains pendant alkyl groups off of the linear ethylene skeleton of the molecule, it is preferred that such lower alkyl groups contain 1–4 carbon atoms and most preferably are either methyl or ethyl.

The reaction itself may be carried out by resort to a solvent if desired, though such is not necessary. Typical solvents include pyridine, benzene, tetrahydrofuran, toluene, xylene, chloroform, etc. When a solvent is employed it is most preferred that pyridine be used.

The reaction itself may be carried out over a wide range of time and temperature variables. Normally the reaction is complete at a temperature ranging from about 0° to about 130° C over a period of time ranging from about 1–4 hours to about 10 hours. More often the reaction is run at 20°–100° C at ½–5 hours.

The ratio of pentahalo aromatic reactant to amine may again be varied widely. Normally such ratio falls within the ranges of from about 1:1 to 1:10.

It is quite surprising to discover that even when employing considerable excess amine reactant only one halo atom of the polyhalo aromatic compound was amine substituted via reaction of the invention. One would normally expect polysubstitutiion in such case. Likewise, it was noted that the products of the invention did not further react with another polyhalo aromatic compound to produce a dianiline compound through such a coupling reaction. Again, one would expect further reaction of this type to normally occur.

The following examples illustrate individual preparations of compounds of my invention. It is understood, of course, that these examples are merely illustrative and are not to be construed as limiting the invention.

EXAMPLE I

To a one liter glass reaction flask is charged 100.0 grams (0.36 mole) pentachlorobenzonitrile, 174.0 grams (2.9 moles) ethylenediamine, and 500 ml pyridine. The resultant mixture was refluxed for 90 minutes, diluted with 4 liters of water and finally filtered. When dry, the light tan solid weighed 50.0 grams. Crystallization from chlorobenzene-ether gave colorless, very small needles, having a melting point of 147°–148° C. Based on analytical and spectral data the compound prepared was cyano-N-(2-aminoethyl)-tetrachloroaniline. The product analysed as follows: Calculated for $C_9H_7Cl_4N_3$ (298.99); 36.15% C, 2.36% H, 47.43% Cl, 14.05% N. Found; 13.6% N, 48.2% Cl. The calculated amine number was 3.34 meg/gm and found to be 3.2 meg/gm.

EXAMPLE II

Here, a mixture consisting of 11.0 grams of pentachlorobenzonitrile, 4.2 grams of 2-(2-aminoethoxy)ethanol, and 250 ml. pyridine was reflexed in a glass vessel for 2 hours. Water was added to the reaction mixture, and the aqueous mixture was extracted several times with ether and the combined extracts were dried over magnesium sulfate. After solvent was removed, 8.5 grams of a product was obtained as a light tan solid.

Analytical and spectral data revealed this product as follows:

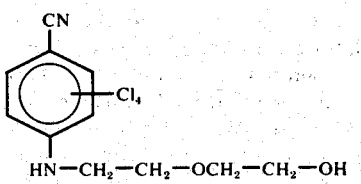

EXAMPLE III

To a warm (60° C) mixture of 200 ml pyridine, 100 ml tetrahydrofuran and 8.4 grams of 2-aminoethanol was added over a period of 20 minutes, 20.0 grams of pentachlorobenzonitrile. After the pale yellow solution had been heated at 80° C for one hour, it was concentrated under reduced pressure and then poured into 2 liters of water. Filtration afforded 20.0 grams of a pale yellow solid identified as cyano-N-(2-hydroxyethyl)-tetrachloraniline.

The product analysed as follows: Calculated for $C_9H_6Cl_4N_2O$ (299.97); 36.03% C, 2.02%H, 47.27% Cl, 9.34% N, 5.33% O. Found; 34.83% C, 1.63% H, 48.8% Cl, 8.89% N.

The products of the invention are particularly useful as biological chemicals and more particularly have utility in controlling undesirable vegetation. Thus, the chemicals here may be both post-emergent herbicides and pre-emergent herbicides depending upon the plant species sought to be controlled. Likewise, the compounds are active fungicides, and particularly exhibit soil fungicidal activity.

FOLIAR FUNGICIDE SCREENING USING EARLY BLIGHT ON TOMATOES

The objective of this test was to evaluate a typical compound of the invention as a foliar fungicide protectant using early blight (*Alternaria solani*) on tomatoes. The compound was applied to tomato foliage (variety Bonnie Best) at a dosage of 500 parts per million (p.p.m.) while the plants were being rotated on a turntable. Effective amounts range from 100 to 500 p.p.m. The spray deposite was allowed to thoroughly dry on the foliage and then sprayed with a spore suspension of *Alternaria solani* again while the plants where being rotated on a turn-table. Immediately after inoculation the plants were transferred to a constant temperature-humidity cabinet for a period of 24 hours. At the end of this time the plants were moved to the greenhouse bench. Final data was recorded 5 to 6 days after incubation at which time the untreated check controls were showing some 150 to 250 early blight leisions per three sets of terminal leaflets per plant. Percent control was recorded as the percentage of leisions occurring on the treated plants over the number of leisions occurring on the untreated controls.

TABLE 1

EVALUATION AS FOLIAR PROTECTANT FUNGICIDES USING EARLY BLIGHT AS THE TEST ORGANISM

| Compound | P.p.m. | Percent early Blight control | Phytotoxicity rating |
|---|---|---|---|
| Example 1 | 500 | 75 | 0 |

We claim:

1. A polyhalo, N-substituted aniline compound having the structural formula

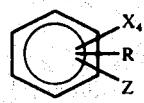

where R is cyano, X is halo, and Z is a radical represented by

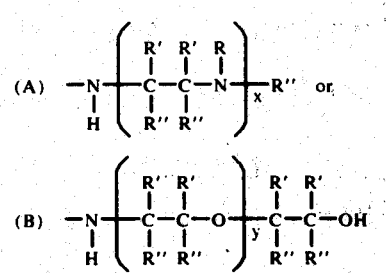

where R' and R" are hydrogen or lower alkyl, $x$ is an integer ranging from 1 to 5 and $y$ is a number of 0–3.

2. The aniline compound of claim 1 where $x$ is chloro.

3. The aniline compound of claim 1 where R' and R" in compound (A) are hydrogen and $x$ is 1.

4. The aniline compound of claim 1 where R' and R" in compound (B) are hydrogen and $y$ is 0.

5. The aniline compound of claim 1 where R and R' in compound (B) are hydrogen and $y$ is 1.

* * * * *